Figure 1:
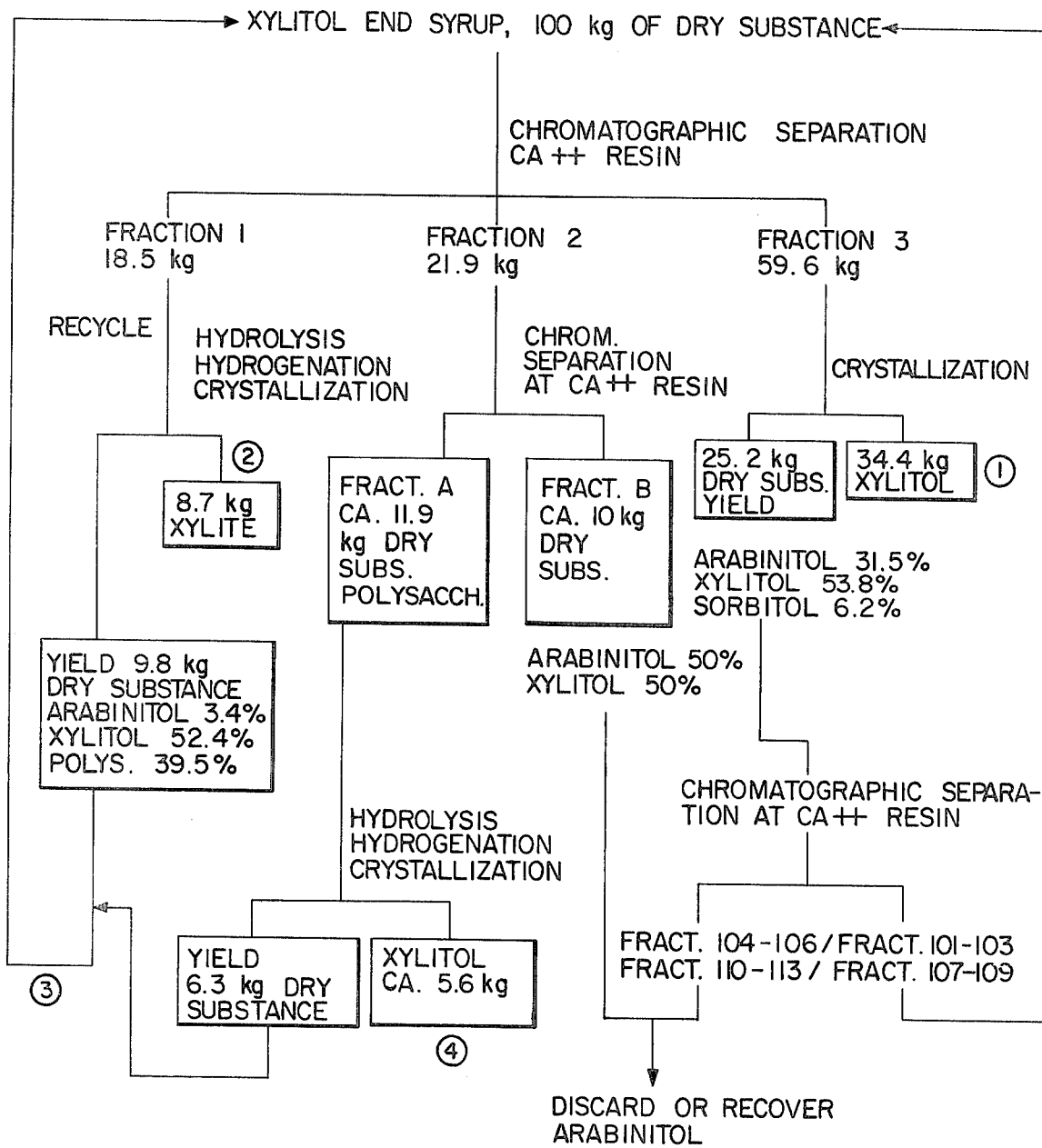

United States Patent [19]

Munir et al.

[11] 4,246,431
[45] Jan. 20, 1981

[54] PROCESS FOR RECOVERING XYLITOL FROM END SYRUPS OF THE XYLITOL CRYSTALLIZATION

[75] Inventors: Mohammad Munir, Obrigheim; Hubert Schiweck, Worms, both of Fed. Rep. of Germany

[73] Assignee: Suddeutsche Zucker-Aktiengesellschaft, Mannheim, Fed. Rep. of Germany

[21] Appl. No.: 47,719

[22] Filed: Jun. 12, 1979

[30] Foreign Application Priority Data

Jun. 14, 1978 [DE] Fed. Rep. of Germany ....... 2826120

[51] Int. Cl.³ ............................................. C07C 31/26
[52] U.S. Cl. ................................... 568/872; 568/863; 127/46 A
[58] Field of Search ............................... 568/872, 863

[56] References Cited

U.S. PATENT DOCUMENTS 4,008,285 2/1977 Melaja et al. ...................... 568/863

FOREIGN PATENT DOCUMENTS 45-37817 11/1970 Japan ...................... 568/863

Primary Examiner—Joseph E. Evans
Attorney, Agent, or Firm—Armstrong, Nikaido, Marmelstein & Kubovcik

[57] ABSTRACT

A process for extracting xylitol from the end syrups of the xylitol crystallization by subjecting the end syrup to chromatographic separation, whereby it will be decomposed into two or more fractions, the first fraction containing mainly the polysaccharides and polysaccharide alcohols and the subsequent fractions containing essentially the pentitols and hexitols.

4 Claims, 5 Drawing Figures

PROCESS FOR RECOVERING XYLITOL FROM END SYRUPS OF THE XYLITOL CRYSTALLIZATION

BACKGROUND OF THE INVENTION

The invention relates to a process for extracting xylitol from the end syrups of the xylitol crystallization.

Presently xylitol recovery is predominantly carried out by subjecting suitable xylaneous raw materials to an acid hydrolysis and, thereupon, extracting with water the sugar that was generated, by purifying and fully desalting the aqueous hydrolysates which then are hydrogenated, whereupon, following new desalting and concentration by evaporation, the xylitol is crystallized in one or more steps out of the water or else obtained by precipitation-crystallization using organic solvents (methanol, ethanol, propanol).

The end syrup recovered in the last crystallization stage is in the form of a mother liquor in a proportion of 5 to 10% by weight based on the starting raw material and still containing from about 30 to 60% xylitol in the dry substance.

It was previously believed that the further crystallization of the xylitol out of the final syrup was or would be prevented mainly by said syrup's content of arabinitol, sorbitol, galacitol, mannitol and other monomeric sugar alcohols, and accordingly processes have been developed which allow separating the monomeric sugar alcohols. Such procedures are described for instance in German Offenlegugnsschriften 2 418 801 and 2 710 374. The latter Offenlegungsschrift explicitly stresses that it is much easier to separate the monomeric sugar alcohols using weakly cross-linked, strongly acidic cation exchangers in the strontium-, aluminum- or iron-salt form than when using such exchangers in the form of calcium salt.

Now, it has been surprisingly found that the crystallization of the xylitol present in the end syrups is not so inhibited by the presence of other monomeric sugar alcohols than by the presence of oligo- and poly-saccharides (xylanes) and of hydrogenated oligo- and polysaccharides (polysaccharide alcohols) which increase the viscosity of the end syrup so that—due to the decreased rate of diffusion for xylitol within the solution and the blocking of the xylitol integration into the crystal lattice—the crystallization will stop.

SUMMARY OF THE INVENTION

It is the object of the invention to utilize the above insight so as to propose a process for extracting xylitol from the end syrups of the xylitol crystallization. The process of the invention is characterized by subjecting the end syrup to chromatographic separation, whereby it will be split into two or more fractions, the first fraction containing mainly the polysaccharides and polysaccharide alcohols and the subsequent fractions containing essentially the pentitols and hexitols, whereby (a) the first fraction predominantly containing oligosaccharides and polysaccharide alcohols is subjected to an acid hydrolysis and following removal of the added acid is hydrogenated, the xylitol being crystallized out of the hydrogenated solution, (b) the xylitol is recovered from one of the subsequent fractions containing mainly xylitol, following partial or nearly complete evaporation of the water, by cooling crystallization or by precipitation crystallization, and (c) ensuing mixed fractions in which xylitol and other sugar alcohols and polysaccharides are present together in varying proportions are subjected to further chromatographic separation.

PREFERRED EMBODIMENTS OF THE INVENTION

Accordingly, the process of the invention is based on separating the di-, tri-, tetra- and higher saccharides from the monomeric sugar alcohols by ion exchange chromatography using weakly crosslinked, strongly acidic cation exchangers in the calcium salt form, whereby the xylitol may be directly crystallized out from the fraction containing the monomeric sugar alcohols.

Further, xylitol may be recovered from the fractions containing the di-, tri-, tetra- and higher saccharides and saccharide alcohols by evaporating such fractions to a dry material content between 15 and 45% and by hydrolyzing in the presence of an acid. The hydrolysis is carried out for instance in 0.5 to 1% sulfuric acid at 100° to 120° C. in a pressure vessel. After 1 to 5 hours, the hydrolysis has progressed to such an extent that the larger part of the saccharides is present in monomeric form, predominantly as xylose. The sulfuric acid, thereupon, is directly removed by percolating the hydrolyzed solution through a weakly basic anion exchanger in the OH− form or it is precipitated out with calcium carbonate as gypsum. Thereupon, the neutral solution, having a dry matter content of about 40%, is hydrogenated using Raney Nickel as the catalyst under known reaction conditions (120° C., 100 bars), and after separating the catalyst, it is fully deionized. The purified solution is concentrated by evaporation and the xylitol is extracted by crystallization. The mother syrup obtained after the xylitol is centrifuged off and since it again contains about 40% of polysaccharides and polysaccharide alcohols it is fed back to the separation equipment.

Contrary to prior knowledge, it was surprisingly found that under the conditions of the invention, that is chromatographic separation in separation columns filled with weakly crosslinked, strongly acidic cation exchangers (divinylbenzene content between 3 and 5%), the calcium salt form of the exchangers is better suited than the strontium- or magnesium-salt form.

The conditions of separation of the invention are as follows:

Proportion of input batch: 0.045 to 0.055 bed volumes of a 50% solution of the end syrup
Eluent: water at 85°–95° C.
Elution temperature: 85° to 95° C.
Linear flow rate: 2 to 6 cm/minute To detect the eluted material at the column outlet, the specific rotation $\alpha_{546.07}^{27}$ (polarization) may be used in addition to the index of refraction $n_D^{27}$, as the specific rotation of the polysaccharides is high, whereas the pentitols and hexitols involved are optically inactive or show only slight specific rotations.

Figure 2:
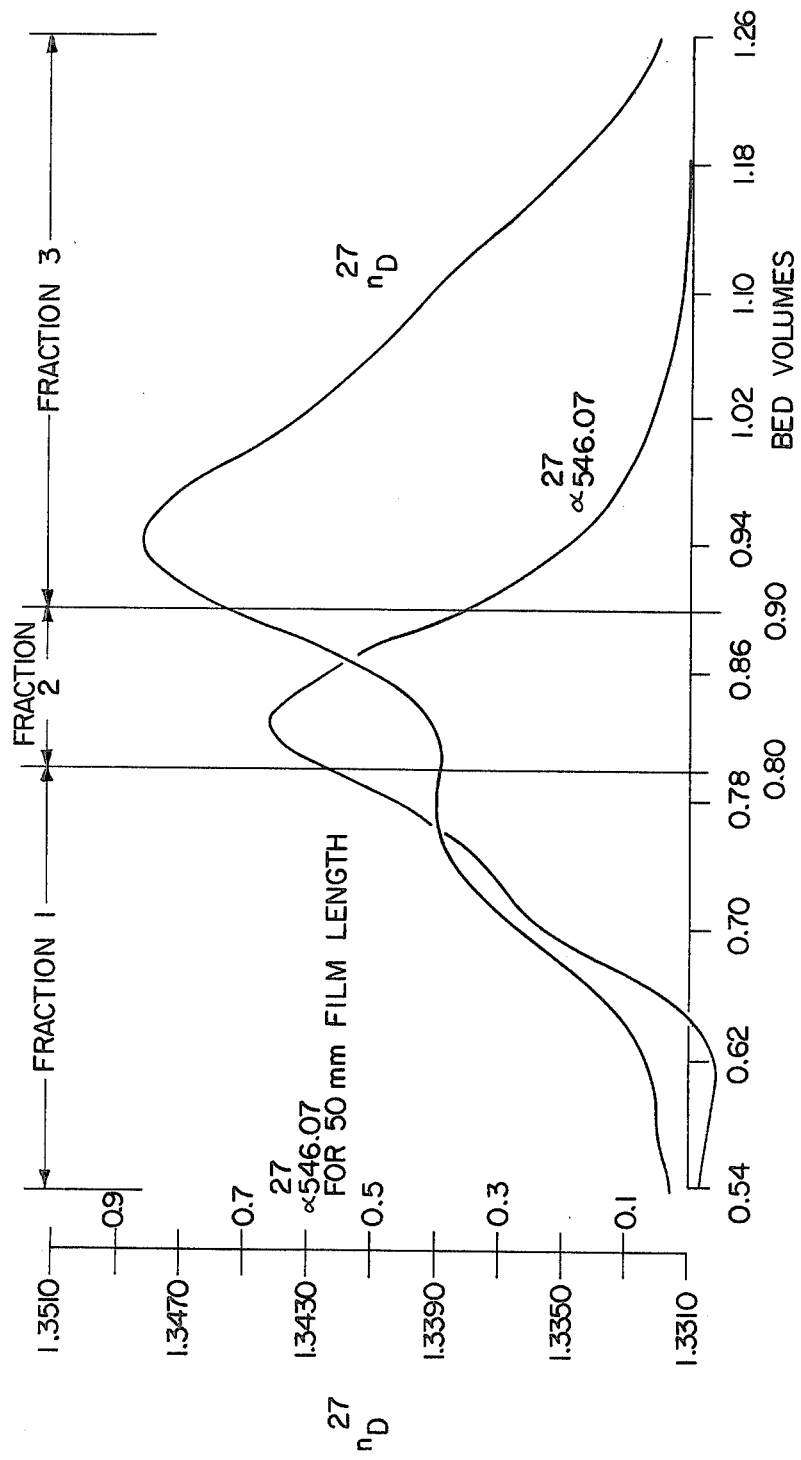

The invention will be illustratively discussed further below, an end syrup being prepared having the following composition:
adonitol 0.6 g/100 g of dry substance
arabinitol 14.0 g/100 g of dry substance
xylitol 46.2 g/100 g of dry substance
mannitol 0.3 g/100 g of dry substance
sorbitol 2.2 g/100 g of dry substance
galactitol 1.0 g/100 g of dry substance oligo- and polysaccharide alcohols 35.7 g/100 g of dry substance FIG. 1 shows the flow and quantitative diagram for the processing of 100 kg of end syrup dry substance of the above composition, in this case the overall eluate being divided into three fractions as shown in FIG. 2 in the chromatographic separation.

The table below shows the compositions of the three fractions:

|  | fraction 1 | fraction 2 | fraction 3 |
|---|---|---|---|
| adonitol % dry substance | — | 2.1 | — |
| arabinitol % dry substance | — | 19.6 | 16.0 |
| xylitol % dry substance | 0.3 | 2.0 | 78.4 |
| mannitol % dry substance | — | 1.2 | — |
| sorbitol % dry substance | — | — | 3.7 |
| galactitol % dry substance | — | 0.3 | 1.0 |
| oligo- and poly-saccharide alcohols % dry substance | 99.7 | 74.8 | 0.9 |

A separation facility for chromatographic separation was used, which consisted of three columns in series, each 25 cm in diameter and 3.20 meters long, the overall column length therefore being 9.60 meter, the columns being filled with strongly acidic, weakly crosslinked (4% divinylbenzene) cation exchanger in the calcium salt form (overall about 500 liters of resin). 15 kg of end-syrup dry-substance in the form of a 50% solution were used for each cycle; eluation took place with water at 90° C. and a flow rate of 100 liters/hour.

Detection of the product flow at the end of the separation facility was implemented in a continuous manner by an automatic refractometer and an automatic polarimeter. For more precise analysis, the eluate flow was further divided into 20-liter fractions which were tested for their saccharide composition following concentration by evaporation to about 50% dry substance. Several cycles were carried out under the stated conditions, the substance being divided into three fractions and these were purified and further processed.

Fraction 1 was concentrated by evaporation to 25% dry substance, and sulfuric acid was added until a 0.5% $H_2SO_4$ solution was obtained, whereupon all of the material was hydrolyzed for 5 hours at 95° C.

The hydrolysate was neutralized with $CaCO_3$, then filtered and concentrated by evaporation to a dry matter content of 50%. The solution was hydrogenated in the presence of a Raney Nickel catalyst at 120° C. and hydrogen at 100 bars pressure. The absorption of hydrogen was complete after 2 hours.

Following cooling, the Raney Nickel catalyst was removed by centrifuging, the solution—containing 58.1% of dry xylitol and 2.2% of dry arabinitol—was fully deionized and, following concentration by evaporation to 85% of dry-substance content, was subjected to cooling crystallization. The xylitol yield upon the amount of dry substance subjected to crystallization, was 46.8%. As 18.5% of the original xylitol-mother liquor-dry substance during separation had passed into fraction 1, the additional xylitol yield was 8.7% of the initial xylitol-mother liquor-dry substance.

The mother liquor obtained following separation of the crystals had the following composition:
adonitol 1.0% dry substance
arabinitol 3.4
xylitol 52.4
mannitol 1.0
sorbitol 1.0
galacitol 1.7
oligo- and polysaccharide alcohols 39.5

The high content of oligo- and polysaccharides increases the viscosity of the solution and prevents xylitol from crystallizing. This run is fed back to a further separation step and a further amount of xylitol is thus obtained. In this manner, it becomes feasible to extract about 70% of the dry substance content as xylitol in fraction 1.

Figure 3:
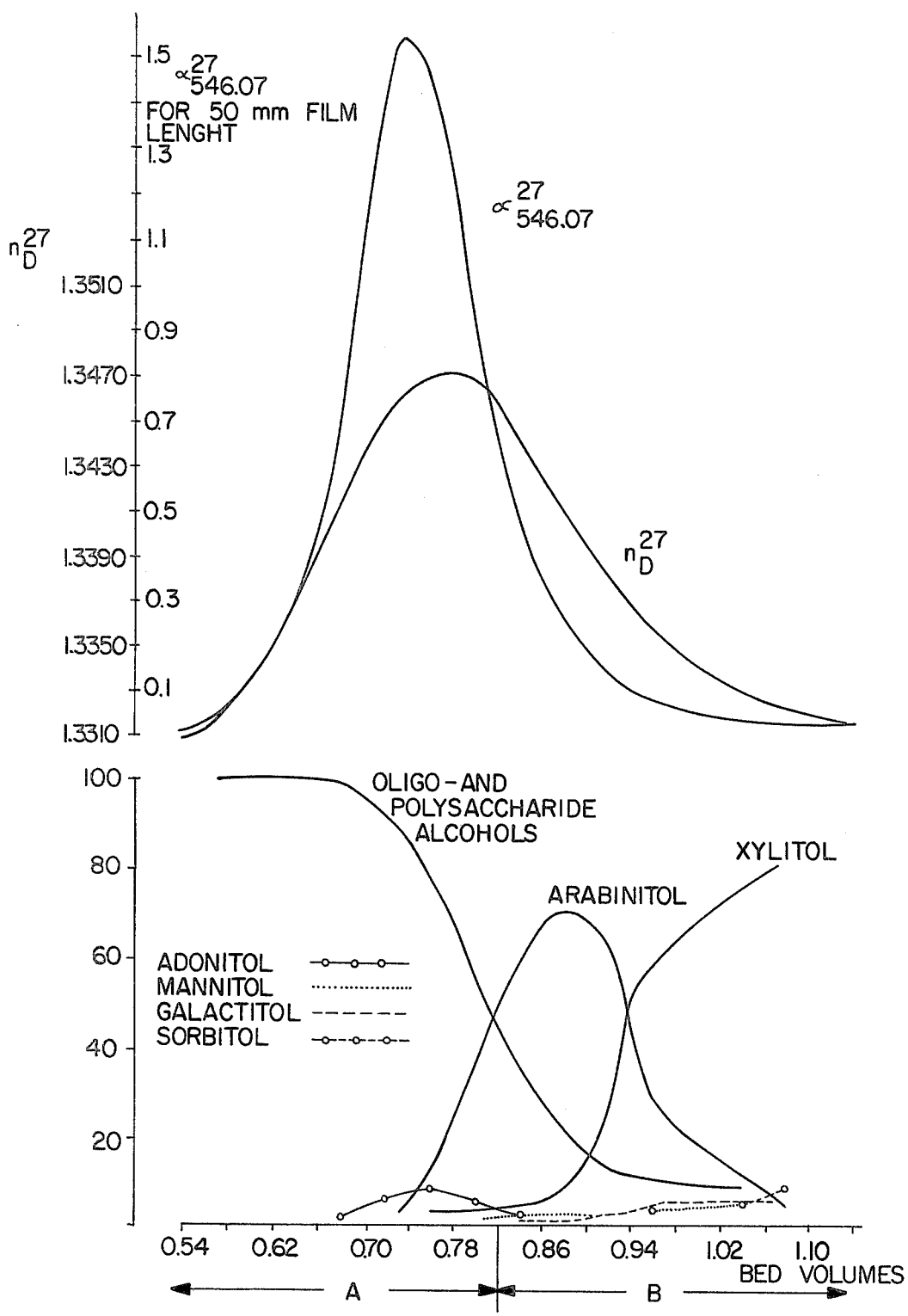

As indicated by the composition of fraction 2, xylitol cannot be directly obtained from the fraction. Therefore, the fractions 2 of several cycles were combined, concentrated by evaporation to 50% dry substance and once more subjected to chromatographic separation in the separation facility described above under the same conditions. The result from this separation is shown in FIG. 3. As indicated, a fraction A is obtained, which consists mainly of only oligo- and polysaccharides, and a fraction B, where arabinitol and xylitol are present in about the same proportions, provided the fractionation of the eluate is carried out at about 0.82 bed volume. In the same way as fraction 1, fraction A is processed alone, or together with fraction 1.

Fraction B can be split into arabinitol and xylitol by a further chromatographic separation.

Fraction 3 was collected from several cycles and concentrated by evaporation to 85% dry-substance content and fed into a cooling crystallizer. The xylitol crystallized out very easily and was readily separated from the mother liquor in a wire basket centrifuge. The crystal yield on the overall amount of dry substance subjected to crystallization, was 57.8%. Accordingly, 34.4% of the initial xylitol-end-syrup/dry-substance could be extracted as crystalline xylitol.

The end syrup obtained after separation was of the following composition:
adonitol -% dry substance
arabinitol 31.5
xylitol 53.8
mannitol -
sorbitol 6.2
galactitol 2.0
oligo- and polysaccharide alcohols 6.3

Figure 4:
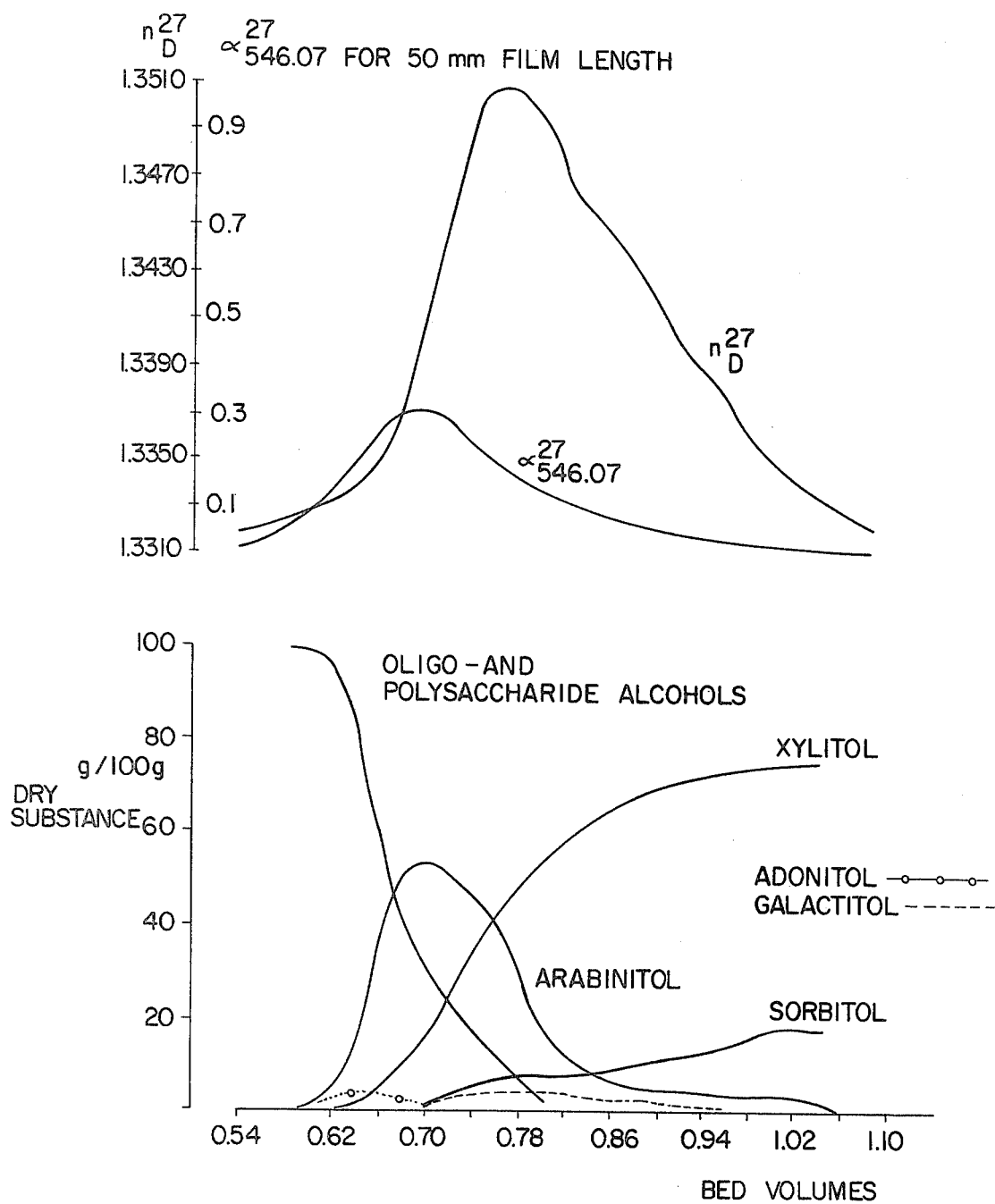

This end syrup was subjected to another chromatographic separation under the conditions described above and split into fractions 101 through 114. FIG. 4 shows the compositions of the fractions and Table 1 shows the saccharide compositions of the individual fractions.

TABLE 1

| Fraction | 101 | 102 | 103 | 104 | 105 | 106 | 107 | 108 | 109 | 110 | 111 | 112 | 113 |
|---|---|---|---|---|---|---|---|---|---|---|---|---|---|
| Bed volumes | 0.56 | 0.60 | 0.64 | 0.68 | 0.72 | 0.76 | 0.80 | 0.84 | 0.88 | 0.92 | 0.96 | 1.00 | 1.04 |
| Adonitol | — | — | 3.2 | 1.9 | — | — | — | — | — | — | — | — | — |
| Arabinitol | — | 0.1 | 14.7 | 50.5 | 49.3 | 39.1 | 15.8 | 7.8 | 4.9 | 2.5 | 2.0 | 2.0 | 1.2 |
| Xylitol | — | — | 0.9 | 19.2 | 28.2 | 41.8 | 71.7 | 83.9 | 84.8 | 86.4 | 84.5 | 80.9 | 81.8 |
| Mannitol | — | 0.1 | 0.8 | 1.6 | — | — | — | — | — | — | — | — | — |
| Sorbitol | — | — | — | — | 2.6 | 5.0 | 5.1 | 7.0 | 8.8 | 10.0 | 12.8 | 16.4 | 16.4 |
| Galactitol | — | — | — | 1.4 | 2.1 | 2.5 | 3.0 | 1.2 | 1.5 | 0.6 | 0.5 | 0.7 | — |

TABLE 1-continued

| Fraction | 101 | 102 | 103 | 104 | 105 | 106 | 107 | 108 | 109 | 110 | 111 | 112 | 113 |
| --- | --- | --- | --- | --- | --- | --- | --- | --- | --- | --- | --- | --- | --- |
| Bed volumes | 0.56 | 0.60 | 0.64 | 0.68 | 0.72 | 0.76 | 0.80 | 0.84 | 0.88 | 0.92 | 0.96 | 1.00 | 1.04 |
| Σ | — | 0.2 | 19.6 | 74.6 | 82.2 | 88.4 | 95.6 | 99.9 | 100 | 99.5 | 99.8 | 100 | 99.4 |
| Oligo- and polysaccharide alcohols | 100 | 99.8 | 80.4 | 25.4 | 17.8 | 11.3 | 4.6 | — | — | — | — | — | — |
| Σ | 100 | 100 | 100 | 100 | 100 | 99.7 | 100.2 | 99.9 | 100 | 99.5 | 99.8 | 100 | 99.4 |

As represented in FIG. 1, fractions 104 through 106 and 110 through 113 are discarded or else are used as the raw material for recovering arabinitol, whereas fractions 101 through 103 and 107 through 109 are fed back.

Figure 5:
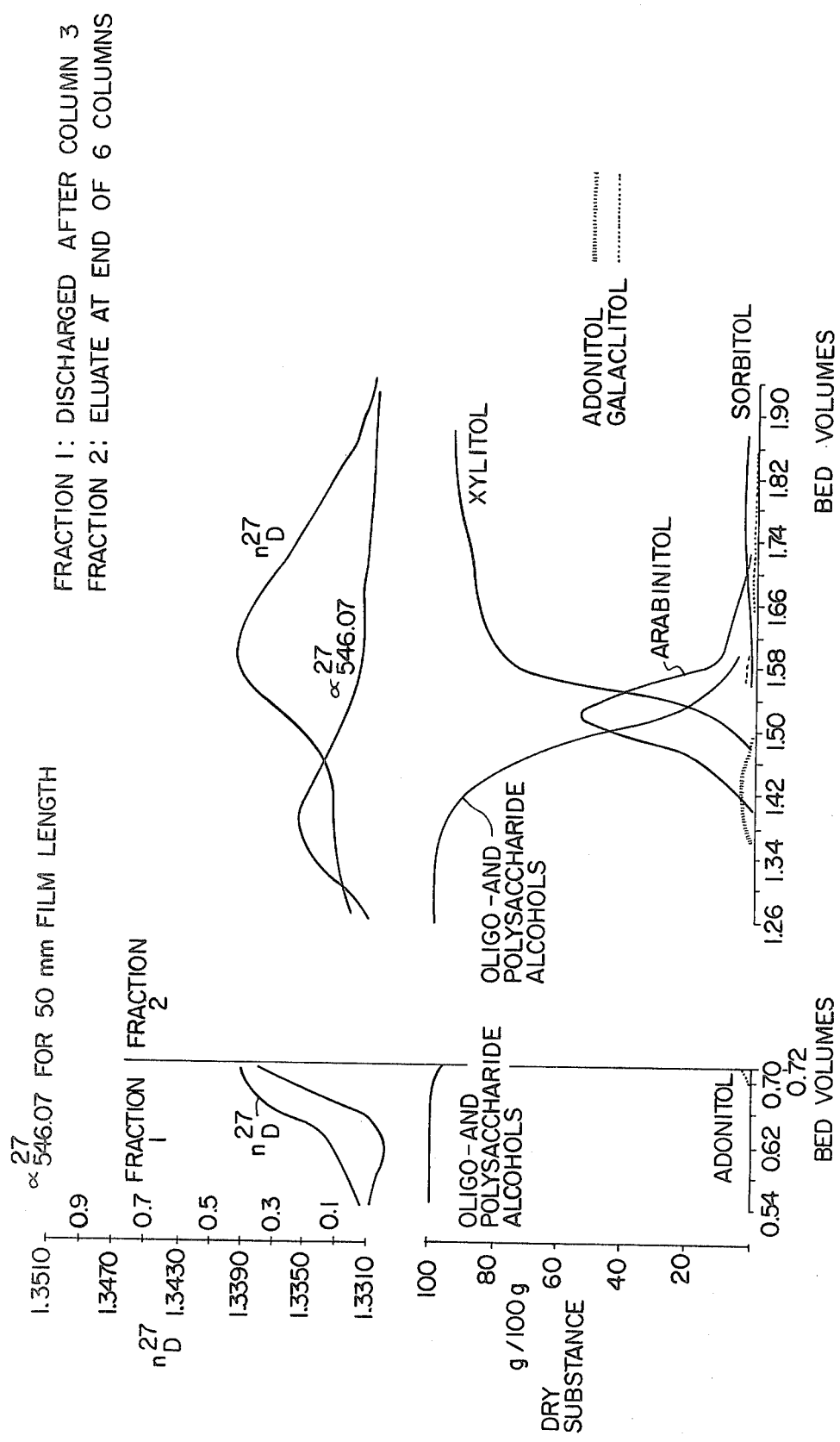

If instead of 3 separating columns in series as in the example above, 6 separating columns are arranged in series, and if part of the polysaccharides are already removed from the facility at the end of the 3rd separating column, then a practically complete separation of the polysaccharides can be achieved in a single separation procedure, as shown by FIG. 5. Furthermore, an extended length of the separation columns permits good separation of the arabinitol from the xylitol.

In view of the insights gained, it seems appropriate to try hydrolyzing the polysaccharides prior to chromatographic separation. Results in that direction when using acid hydrolysis show that the hydrolysis is insufficient in this approach. For instance, acid hydrolysis in 0.5% sulfuric acid of a solution with a substance content of 25% yields, a reduction value of 12.6% on dry substance (value for glucose=100%) after 2 hours at 100° C., which rose only slightly, to 16%, after 22 hours, but failed to reach the theoretical value of about 35%. Following hydrogenation and corresponding processing of the hydrolyzed solution, it was possible indeed to crystallize part of the xylitol, however, the additional xylitol yield amounted to only 10 to 20% based on the dry substance input, and, therefore, was well below the value for the above described process of the invention.

What is claimed is:

1. A process for recovering xylitol from end syrups of xylitol crystallization, characterized by subjecting the end syrup to chromatographic separation using a weakly crosslinked, strongly acidic cation exchanger in the calcium salt form and splitting the syrup into at least three fractions, a first fraction containing predominantly polysaccharides and polysaccharide alcohols, a mixed fraction, and a subsequent fraction containing essentially pentitols and hexitols, the process comprising:
    (a) subjecting the first fraction to acid hydrolysis,
    (b) removing the acid,
    (c) hydrogenating the fraction and crystallizing xylitol from the hydrogenated fraction,
    (d) evaporating water partially or nearly completely from said subsequent fraction and separating xylitol from the evaporated subsequent fraction containing predominantly xylitol by cooling crystallization or precipitation crystallization, and
    (e) subjecting said mixed fraction in which xylitol and other sugar alcohols and polysaccharides are present in varying proportions to further chromatographic separation.

2. The process according to claim 1, wherein the chromatographic separation is accomplished at a temperature of from 85° to 90° C. and at a linear flow rate of 2 to 6 cm/minute using deionized water as the eluent.

3. The process according to claim 1, wherein the first fraction contains polysaccharides/polysaccharide-alcohols having a dry substance content of 15 to 40% by weight and is hydrolyzed with 0.5 to 1% sulfuric acid at a temperature of from 100° to 120° C. in the absence or presence of pressure for a time between 1 and 5 hours.

4. The process according to claim 1, wherein the mixed fraction obtained by separating xylitol according to one of claims 1 through 3 are subjected to still further chromatographic separation.

* * * * *